(12) United States Patent
Hampton et al.

(10) Patent No.: US 10,364,250 B2
(45) Date of Patent: Jul. 30, 2019

(54) BIOACTIVE COMPOUNDS

(71) Applicants: Mark Barry Hampton, Christchurch (NZ); Andrew Ian Selwood, Nelson (NZ); Feng Shi, New South Wales (AU)

(72) Inventors: Mark Barry Hampton, Christchurch (NZ); Andrew Ian Selwood, Nelson (NZ); Feng Shi, New South Wales (AU)

(*) Notice: Subject to any disclaimer, the term of this patent is extended or adjusted under 35 U.S.C. 154(b) by 0 days.

(21) Appl. No.: 15/314,258

(22) PCT Filed: May 26, 2014

(86) PCT No.: PCT/NZ2014/000096
§ 371 (c)(1),
(2) Date: Nov. 28, 2016

(87) PCT Pub. No.: WO2014/189393
PCT Pub. Date: Nov. 27, 2014

(65) Prior Publication Data
US 2017/0183357 A1  Jun. 29, 2017

(51) Int. Cl.
C07D 491/22 (2006.01)
A61K 31/395 (2006.01)
A61K 31/357 (2006.01)
A61K 31/4353 (2006.01)

(52) U.S. Cl.
CPC .................. C07D 491/22 (2013.01)

(58) Field of Classification Search
CPC combination set(s) only.
See application file for complete search history.

(56) References Cited

U.S. PATENT DOCUMENTS

2012/0245223 A1  9/2012  Botana López et al.

OTHER PUBLICATIONS

By Selwood et al. "Portimine: a bioactive metabolite from the benthic dinoflagellate Vulcanodinium rugosum" Tetrahedron Lett. 2013, 54, 4705-4707 (Year: 2013).*
Kohl et al. "BH3 mimetic ABT-737 neutralizes resistance to FLT3 inhibitor treatment mediated by FLT3-independent expression of BCL2 in primary AML blasts" Leukemia 2007, 21, 1763-1772. (Year: 2007).*
Lu, Chung-Kuang, et al; "Spiro-prorocentrimine, a novel macrocyclic lactone from a benthic *Prorocentrum* sp. of Taiwan"; *Tetrahedron Letters*; 42; pp. 1713-1716 (2001).
Pelc. Matthew, J., et al; "An Approach to the Imine Ring System of Pinnatoxins"; *Organic Letters*, vol. 0. No. 0, pp. A-C; (2005).
Selwood, Andrew I., et al; "Portimine: a bioactive metabolite from the benthic dinoflagellate *Vulcanodinium rugosum*"; *Tetrahedron Letters*, 54; pp. 4705-4707 (2013).

Guéret, Stéphanie M., et al; "Synthetic studies toward the spiroimine unit of the spirolides"; *Pure Appl. Chem.*, vol. 83, No. 3, pp. 425-433 (2011).
Selwood, Andrew I., et al; "Pinnatoxin H: a new pinnatoxin analogue from a South China Sea Vulcanodinium rugosum isolate"; *Tetreahedron Letters*, vol. 55, Issue 40, pp. 5508-5510 (2014); http://www.sciencedirect.com/science/article/pii/S0040403914013902.
International Search Report issued in PCT/NZ2014/000096 dated Nov. 24, 2014.
International Preliminary Report on Patentability issued in PCT/NZ2014/000096 dated Nov. 29, 2016.
Billard (2013) "BH3 Mimetics: Status of the Field and New Developments" *Mol Cancer Ther* 12 (9), 1691-1700.
**Cembella and Krock (2008) In Seafood and Freshwater Toxins: pharmacology, physiology and detection; Botana, L. M., Ed.; CRC Press: Boca Raton, FL; pp. 561-580.
Chipuk et al (2010) "The BCL-2 family reunion" *Molecular Cell*, 37(3), 299-310.
Feher and Schmidt (2003) "Property Distributions: Differences between Drugs, Natural Products, and Molecules from Combinatorial Chemistry" *J. Chem. Inf. Comput. Sci.*, 43, 218-227.
Fuchs and Steller (2011) "Programmed Cell Death in Animal Development and Disease" *Cell*, 147, 742-758.
Hampton and Orrenius (1997) "Dual regulation of caspase activity by hydrogen peroxide: implications for apoptosis" *FEBS letters*, 414(3), 552-556.
Hellyer et al (2011) "Marine algal pinnatoxins E and F cause neuromuscular block in an in vitro hemidiaphragm preparation" *Toxicon*, 58, 693-699.
Hu et al (1995) "Spirolides B and D, Two Novel Macrocycles Isolated from the Digestive Glands of Shellfish" *J. Chem. Soc, Chem. Commun.*, 1995, 2159-2161.
Kharrat et al (2008) "The marine phycotoxin gymnodimine targets muscular and neuronal nicotinic acetylcholine receptor subtypes with high affinity" *Journal of Neurochemistry*, 107(4), 952-963.

(Continued)

*Primary Examiner* — Amanda L Aguirre
(74) *Attorney, Agent, or Firm* — Nixon & Vanderhye P.C.

(57) ABSTRACT

Congener of portimine of the structure:

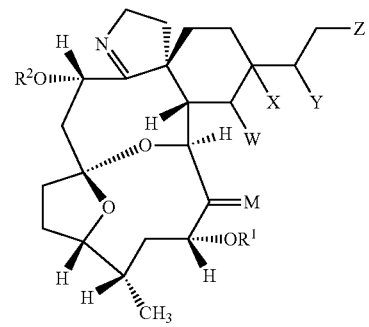

where: $R^1$ is selected from H, acyl, alkyl, alkylene, aryl and aralkyl; $R^2$ is selected from H, acyl, alkyl, alkylene, aryl and aralkyl; M is O, S, N—$NH_2$, N(alkyl)$_2$, N-alkoxy or N(aryl)$_2$; W and X may form a bond, an epoxide, or are independently selected from H, halogen, OH and O-acyl. Y and Z form a bond, an epoxide, or are independently selected from H, halogen (X), OH and O-acyl; and R1 and R2 are not H, M is not O, or W and X or Y and Z do not form a bond.

18 Claims, 7 Drawing Sheets

(56) References Cited

OTHER PUBLICATIONS

Kita and Uemura (2005) "Iminium Alkaloids from Marine Invertebrates: Structure, Biological Activity, and Biogenesis" *Chemistry Letters*, 34, 454-459.

Kita et al (2005) "Symbioimine and neosymbioimine, amphoteric iminium metabolites from the symbiotic marine dinoflagellate *Symbiodinium* sp." *Bioorganic & Medicinal Chemistry*, 13, 5253-5258.

Letai et al (2004) "Antiapoptotic BCL-2 is required for maintenance of a model leukemia" *Cancer Cell*, 6(3), 241-249.

Lu et al (2001) "Spiro-prorocentrimine, a novel macrocyclic lactone from a benthic *Prorocentrum* sp. of Taiwan" *Tetrahedron Letters*, 42, 1713-1716.

McCarron et al (2012) "Identification of Pinnatoxins and Discovery of Their Fatty Acid Ester Metabolites in Mussels (*Mytilus edulis*) from Eastern Canada" *J. Agric. Food Chem.*, 60, 1437-1446.

McNabb et al (2012) "New perspectives on biotoxin detection in Rangaunu Harbour, New Zealand arising from the discovery of pinnatoxins" *Harmful Algae*, 13, 34-39.

Molinski et al (2009) "Drug development from marine natural products" *Nature reviews—Drug discovery*, 8, 69-85.

**Munday (2008) In Seafood and Freshwater Toxins: pharmacology, physiology and detection; Botana, L. M., Ed.; CRC Press: Boca Raton, FL; pp. 581-594.

Munday et al (2012) "Acute toxicity of pinnatoxins E, F and G to mice" *Toxicon*: Official journal of the International Society on Toxicology, 60(6), 995-999.

Nezan and Chomerat (2010) "*Vulcanodinium rugosum* gen. et sp. nov. (Dinophyceae), un nouveau dinoflagellé marin de la côte méditerranéenne française" *Cryptogam. Algol.*, 32 (1), (w/ abstract).

Oltersdorf et al (2005) "An inhibitor of Bcl-2 family proteins induces regression of solid tumours" *Nature*, 435(7042), 677-681.

Rhodes et al (2011) "Dinoflagellate Vulcanodinium rugosum identified as the causative organism of pinnatoxins in Australia, New Zealand and Japan" *Phycologia*, 50, 624-628.

Roach et al (2009) "Characterization of a Dispiroketal Spirolide Subclass from *Alexandrium ostenfeldii*" *J. Nat. Prod.*, 72, 1237-1240.

Seki et al (1995) "Gymnodimine, a New Marine Toxin of Unprecedented Structure Isolated from New Zealand Oysters and the Dinoflagellate, *Gymnodinium* sp." *Tetrahedron Lett.* 36, 7093-7096.

Selwood et al (2010) "Isolation, Structural Determination and Acute Toxicity of Pinnatoxins E, F and G" *J. Agric. Food Chem.*, 58, 6532-6542.

Selwood et al (2013) "Portimine: a bioactive metabolite from the benthic dinoflagellate *Vulcanodinium rugosum*" *Tetrahedron Letters*, 54(35), 4705-4707.

Shi (2012) "Chemical and toxicological investigation of the toxic dinoflagellate, *Karenia brevisulcata*" Doctoral (Ph.D.) thesis, Lincoln University, Christchurch, http://hdl.handle.net/10182/4547.

Sleno et al (2004) "Structural study of spirolide marine toxins by mass spectrometry" *Anal. Bioanal. Chem.*, 378, 969-976.

Takada et al (2001) "Structural determination of pteriatoxins A, B and C, extremely potent toxins from the bivalve *Pteria penguin*" *Tetrahedron Lett.*, 42, 3495-3497.

Tanaka et al (2013) "Discovery of potent Mcl-1/Bcl-xl dual inhibitors by using a hydribization strategy based on structural analysis of target proteins" *J. Medicinal Chem.*, 56, 9635-9645.

Thomson et al (2006) "Phenethyl isothiocyanate triggers apoptosis in Jurkat cells made resistant by the overexpression of Bcl-2" *Cancer Research*, 66, 6772-6777.

Torigoe et al (1988) "Prorocentrolide, a Toxic Nitrogenous Macrocycle from a Marine Dinoflagellate, *Prorocentrum lima*" *J. Am. Chem. Soc.*, 110, 7876-7877.

Uemura et al (1995) "Pinnatoxin A: A Toxic Amphoteric Macrocycle from the Okinawan Bivalve *Pinna muricata*" *J. Am. Chem. Soc.*, 117, 1155-1156.

Van Delft et al (2006) "The BH3 mimetic ABT-737 target selective Bcl-2 proteins and efficiently induces apoptosis via Bak/Bax if Mcl-1 is neutralized" *Cancer Cell*, 10(5), 389-399.

Van Wagoner et al (2011) "Occurrence of 12-methylgymnodimine in a spirolide-producing dinoflagellate *Alexandrium peruvianum* and the biogenetic implications" *Tetrahedron Lett.*, 52 (33), 4243-4246.

Zhou et al (2012) "Structure-based design of potent Bcl-2/Bcl-xL inhibitors with strong in vivo antitumor activity" *J. Medicinal Chem.*, 55, 6149-6161.

* cited by examiner

BIOACTIVE COMPOUNDS

This application is the U.S. national phase of International Application No. PCT/NZ2014/000096 filed May 26, 2014 which designated the U.S., the entire contents of each of which are hereby incorporated by reference.

FIELD OF INVENTION

The invention relates to novel bioactive polycyclic ether compounds comprising a spiro-linked five-membered cyclic imine. In particular, the invention relates to the compound I designated portimine, its congeners and the use of these compounds in anticancer therapy.

BACKGROUND ART

Cyclic imines are a group of secondary metabolites produced by marine dinoflagellates that are characterised by spiro-linked cyclic imines, macrocycles and ether rings (Cembella and Krock (2008); Roach et al (2009); Selwood et al (2010); Van Wagoner et al (2011)). Compound families included in this group are spirolides (Hu et al (1995)), pinnatoxins (Uemura et al (1995)), gymnodimines (Seki et al (1995)), pteriatoxins (Takada et al (2001)), prorocentrolides (Torigoe et al (1988)), spiro-prorocentrimines (Lu et al (2001)) and symbioimines (Kita et al (2005)). In all these compounds, the cyclic imine moiety consists of a six- or seven-membered ring with a spiro-link to a cyclohexene ring.

Pinnatoxin A was first described in 1995 from an Okinawan bivalve (Uemura et al (1995)) and a range of congeners of the compound Pinnatoxin A have since been reported. However, it is only recently that a pinnatoxin-producing benthic microalga, *Vulcanodinium rugosum*, was reported from New Zealand waters (Rhodes et al (2011); Nézan and Chomérat (2010)). Strains of this dinoflagellate have now been found in many locations around the world, including Australia, Japan, China, France and Hawaii.

The toxin profile of *V. rugosum* varies among strains, producing a single pinnatoxin, a mixture of pinnatoxins or no pinnatoxins (Rhodes et al (2011); Nézan and Chomérat (2010)). Shellfish accumulate pinnatoxins and can metabolise them to other analogues including fatty acid esters (McCarron et al (2012)). Administration of pinnatoxins and other cyclic imines to mice leads to death by respiratory failure (Munday (2008)).

Cyclic imines have been shown to block muscular and neuronal nicotinic acetylcholine receptors (Kita and Uemura (2005); Hellyer et al (2011)), and the observed death by asphyxia is consistent with inhibition of neuromuscular transmission, leading to paralysis of the diaphragm. To date there have been no reports of human intoxication by shellfish contaminated with cyclic imines (Kita and Uemura (2005)).

Secondary metabolites produced by marine organisms are recognised as a source of lead compounds for drug development (Molinski et al (2009)). Analyses of the property distributions of drugs, natural products and compounds from combinatorial chemistry have shown a better correlation between those for drugs and natural products, than between those for drugs and compounds from combinatorial chemistry (Feher and Schmidt (2003)).

A target for drug development by rational design is the regulation of apoptosis, otherwise known as programmed cell death. Apoptosis is a cell suicide mechanism by which multicellular organisms remove damaged or unwanted cells in order to maintain normal life development and homeostasis (Fuchs and Steller (2011)).

Members of the BCL-2 family of proteins are functionally classified as either antiapoptotic or proapoptotic. The regulation of the interaction of these proteins dictates survival or commitment to apoptosis. Central to the initiation of apoptosis is the activation at the outer mitochondrial membrane of the proapoptotic BCL-2 family members BAK and BAX. Upon activation these proteins homo-oligomerize into proteolipid pores to promote mitochondrial outer membrane permeabilization. Following mitochondrial outer membrane permeabilization, caspase activation and apoptosis ensue. The caspase proteases effectively package and label dying cells for rapid clearance (Chipuk et al (2010)).

The BCL-2 family of proteins is implicated in a range of diseases of which cancer is the best characterised. A prevalent mechanism of apoptosis dysregulation in cancer is overexpression of antiapoptotic family members, e.g. BCL-2 or BCL-xl in lymphoma and epithelial cancers. Inhibiting the action of these proteins has therefore been used as a target for the development of drugs for use on the treatment of subjects with neoplasia. The compound designated ABT-737 and its orally bioavailable counterpart designated ABT-263 are inhibitors of the antiapoptotic action of BCL-2 family members. The compounds ABT-737 and ABT-263 have been shown to be effective as a synergist or a single agent, respectively, in selectively killing tumour cells (van Delft et al (2006); Oltersdorf et al (2005)).

It is an object of the present invention to provide a standard for use in monitoring the occurrence in the environment or harvested marine organisms of the compound I. It is an object of the present invention to provide lead compounds for drug development. These objects are to be read disjunctively with the object to provide at least a useful choice.

STATEMENT OF INVENTION

In a first aspect the invention provides congeners of the structure:

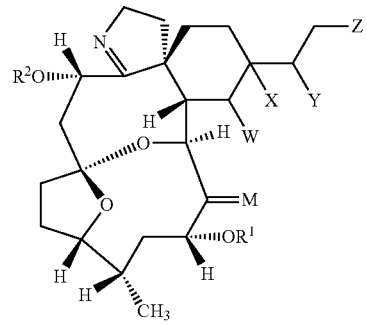

where: $R^1$ and $R^2$ are independently selected from the group consisting of: H, acyl, alkyl, alkylene, aryl or aralkyl; M is O, S, N—$NH_2$, N(alkyl)$_2$, N-alkoxy or N(aryl)$_2$; W and X may form a bond, an epoxide, or are independently selected from the group consisting of: H, halogen (X), OH, O-acyl; and Y and Z may form a bond, an epoxide, or are independently selected from the group consisting of: H, halogen (X), OH, O-acyl.

Preferably, $R^1$ and $R^2$ are unsubstituted.
Preferably, the congeners are semisynthetic compounds.
Preferably, the congeners are differentially toxic.

Preferably, the congeners are differentially toxic, semi-synthetic compounds.

In a first preferment of the first aspect the invention provides congeners of the structure:

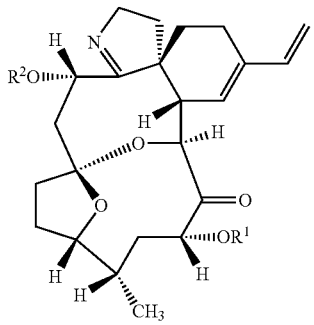

where $R^1$ and $R^2$ are independently selected from the group consisting of: H, acyl, alkyl, alkylene, aryl or aralkyl. Preferably, $R^1$ and $R^2$ are unsubstituted.

In a second preferment of the first aspect the invention provides congeners of the structure:

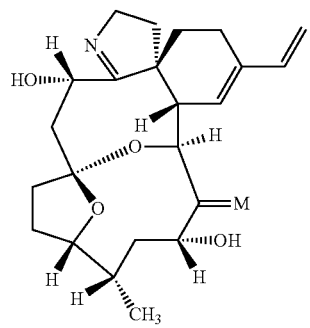

where M is O, S, N—$NH_2$, N(alkyl)$_2$, N-alkoxy or N(aryl)$_2$.

In a third preferment of the first aspect the invention provides congeners of the structure:

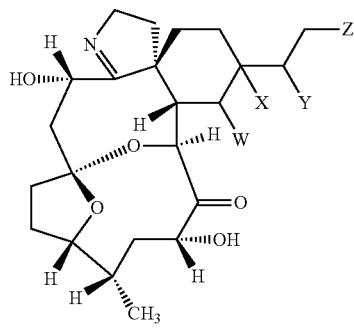

where: W and X may form a bond, an epoxide, or are independently selected from the group consisting of: H, halogen (X), OH, OCOAlkyl; and Y and Z may form a bond, an epoxide, or are independently selected from the group consisting of: H, halogen (X), OH, OCOAlkyl.

In an embodiment of the first aspect the invention provides compound I of the structure:

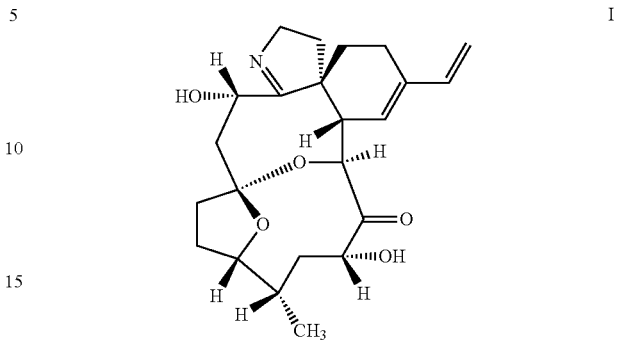

((4R,6S,9R,10R,12S,14R,14aR,18aS)-rel-16-ethenyl-1,2,4,5,7,8,9,10,11,12, 14,14a,17,18-tetradecahydro-4,12-dihydroxy-10-methyl-)13H-6,9:6,14-diepoxybenzo[2,3]cyclotetradeca[1,2-b]pyrrol-13-one) ("portimine").

In a second aspect the invention provides a pharmaceutical preparation comprising as active ingredient a congener of the first aspect of the invention. Preferably, the pharmaceutical preparation is indicated for use in the treatment of subjects with neoplasia. More preferably, the pharmaceutical preparation is indicated for use in the treatment of subjects with lymphoid malignancies. Preferably, the lymphoid malignancies are selected from the group consisting of: chronic lymphocytic leukaemia (CLL) and pediatric acute lymphoblastic leukaemia (ALL).

In a third aspect the invention provides the use of a congener of the first aspect of the invention as a synergist for an antagonist of antiapoptotic proteins. Preferably, the antagonist of antiapoptotic proteins is a BH3 mimetic. More preferably, the antagonist of antiapoptotic proteins is a BH3 mimetic selected from the group consisting of: 4-[4-[[2-(4-chlorophenyl)-4,4-dimethyl-1-cyclohexen-1-yl]methyl]-1-piperazinyl]-N-[[3-nitro-4-[[(tetrahydro-2H-pyran-4-yl)methyl]amino]phenyl]sulfonyl]-2-(1H-pyrrolo [2,3-b]pyridin-5-yloxy)-benzamide (ABT-199); 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]-benzamide (ABT-263); 4-[4-[(4'-chloro[1,1'-biphenyl]-2-yl)methyl]-1-piperazinyl]-N-[[4-[[(1R)-3-(dimethylamino)-1-[(phenylthio) methyl]propyl]amino]-3-nitrophenyl]sulfonyl]-benzamide (ABT-737); (R)-5-(4-chlorophenyl)-4-(3-(4-(4-(4-((4-(dimethylamino)-1-(phenylthio) butan-2-yl)amino)-3-nitrophenylsulfonamido)-phenyl)piperazin-1-yl)phenyl)-1-ethyl-2-methyl-1H-pyrrole-3-carboxylic acid (14, Zhou et al (2012)); (R)-5-(4-chlorophenyl)-4-(3-(4-(4-(4-((4-(dimethylamino)-1-(phenylthio)butan-2-yl)-amino)-3-nitrophenylsulfonamido)-phenyl)piperazin-1-yl)phenyl)-1-isopropyl-2-methyl-1H-pyrrole-3-carboxylic acid (15, Zhou et al (2012)); (R)-7-(4-(((4-((4-(dimethylamino)-1-(phenylthio)butan-2-yl)-amino)-3-nitrophenyl)sulfonyl)carbamoyl)-2-methylphenyl)-3-(3-(naphthalen-1-yloxy)propyl) pyrazolo[1,5-α]pyridine-2-carboxylic acid (10, Tanaka et al (2013)); and (R)-7-(4-(((4-((4-(dimethylamino)-1-(phenylthio)butan-2-yl)-amino)-3-nitrophenyl)sulfonyl)carbamoyl)-2,6-dimethylphenyl)-3-(3-(naphthalen-1-yloxy)propyl) pyrazolo[1,5-α]pyridine-2-carboxylic acid (11, Tanaka et al (2013)). Most preferably, the antagonist of antiapoptotic proteins is the BH3 mimetic 4-[4-[(4'-chloro[1,1'-biphenyl]-2-yl)methyl]-1-piperazinyl]-N-[[4-[[(1R)-3-(dimethylamino)-1-[(phenylthio) methyl]propyl]amino]-3-nitrophenyl]sulfonyl]-benzamide (ABT-737).

In the description and claims of this specification the following acronyms, terms and phrases have the meaning provided: "acyl" means a radical formed from an organic acid by removal of a hydroxyl group; "alkoxy" means a alkyl radical attached to a molecule by oxygen, e.g. ethoxy; "alkyl" means a monovalent radical which may be considered to be formed by the loss of a hydrogen atom from an alkane, e.g. ethyl (from ethane); "alkylene" means a radical formed from an unsaturated aliphatic hydrocarbon, e.g. ethylene; "aryl" means a monovalent radical derived from an aromatic hydrocarbon by removal of one hydrogen, e.g. benzyl (from benzene); "aralkyl" means a radical in which an aryl group is substituted for a hydrogen of an alkyl; "comprising" means "including", "containing" or "characterized by" and does not exclude any additional element, ingredient or step; "consisting of" means excluding any element, ingredient or step not specified except for impurities and other incidentals; "cytotoxic" means induces damage to cellular macromolecules (leading to necrosis); "differential toxicity" means the compound has an $LD_{50}$ in mice by intraperitoneal injection of greater than 1,500 μg/Kg and an $EC_{50}$ in mammalian cell culture (P388 and Vero cells) of less than 5 nmol and "differentially toxic" has a corresponding meaning; "neoplasia" means abnormal cell growth, "pharmaceutical preparation" means a preparation comprising pharmaceutically acceptable excipients in addition to one or more active ingredients; "selective" means induces apoptosis at concentrations that are not cytotoxic and "semi-synthetic" means prepared by chemical modification of a parent compound of biological origin.

Congeners of the compound I are compounds comprising the substructure:

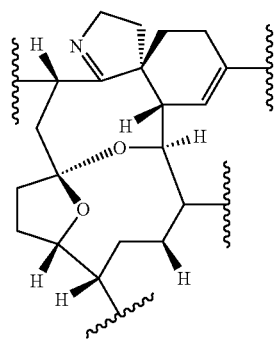

The terms "first", "second", "third", etc. used with reference to elements, features or integers of the subject matter defined in the Statement of Invention and Claims, or when used with reference to alternative embodiments of the invention are not intended to imply an order of preference.

Where concentrations or ratios of reagents are specified the concentration or ratio specified is the initial concentration or ratio of the reagents. Where values are expressed to one or more decimal places standard rounding applies. For example, 1.7 encompasses the range 1.650 recurring to 1.7499 recurring.

The invention will now be described with reference to embodiments or examples and the figures of the accompanying drawings pages.

DETAILED DESCRIPTION

Figure 1:
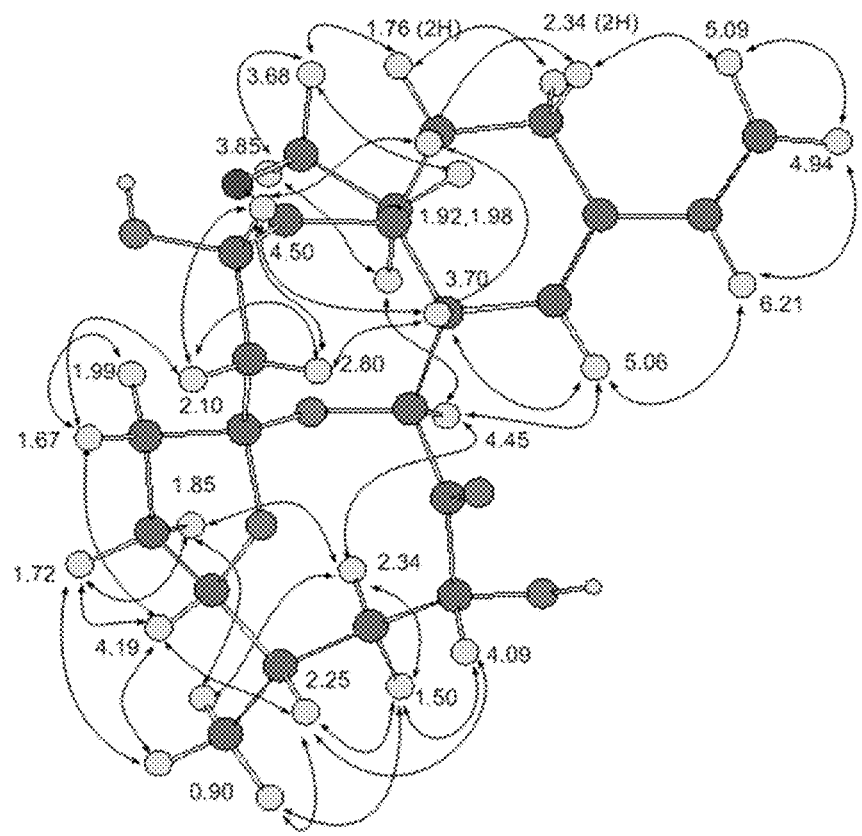
FIG. 1. NOE correlations observed for the compound I designated portimine ($^{1}$H resonances are marked).

During isolation of pinnatoxins from *V. rugosum*, a nitrogen-containing compound [M+H]+m/z 402 was observed. The compound I was designated portimine after *Portodinium honu*, a preliminary name for *V. rugosum*. The structure of portimine (with the positions of carbons numbered) was elucidated to be:

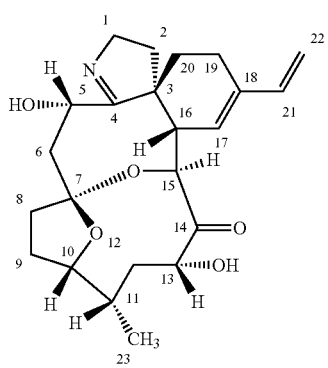

I

The compound I is a bioactive cyclic imine with an unprecedented five-membered imine ring. The compound I has few structural similarities to other polycyclic ether toxins including those produced by *V. rugosum* such as pinnatoxin-E or pinnatoxin-F. The compound I is of comparatively low toxicity to mice, but highly toxic to mammalian cells in vitro, appearing to be apoptogenic in P388 cells. Whilst not wishing to be bound by theory it is believed that this differential toxicity may be attributable to the presence of the five-membered imine ring. It is further anticipated that the compound I and its congeners will have utility as lead compounds in the development of active or synergistic ingredients for pharmaceutical preparations indicated for use in the treatment of subjects with neoplasia. In such development and use it is advantageous if the parent compound is produced by a culturable organism. An inability to produce the parent compound in sufficient quantities is a major impediment to development and use. It has been observed that portimine is commonly produced by isolates of *V. rugosum* and may therefore be produced in culture.

Production of the Compound I Designated Portimine

Cells from a culture of the species *Vulcanodinium rugosum* (60 L, $1.2\times10^5$ cells) were harvested, lyophilised and extracted with MeOH. The dried residue (2.4 g) was successively partitioned between $EtOH/H_2O$ (1:1) and n-hexane followed by EtOAc. The EtOAc extract (1.2 g) was subjected to open chromatography on a silica gel column and two stages of solid phase extraction (SPE) purification (Strata-X), followed by C18-reversed phase HPLC with an acidic mobile phase. A final stage of SPE under basic conditions yielded the free base of the compound I as a white amorphous solid (12.5 mg).

Initial Characterisation and Use of the Compound I as an Analytical Standard

Structural Characteristics

The molecular formula of was established as $C_{23}H_{31}NO_5$ from the ESI-TOFMS [$(M+H)^+$ observed, 402.2267; required for $C_{23}H_{32}NO_5$. 402.2275; 9 rings plus double bonds].

The $^1$H NMR spectrum of the compound I in $CDCl_3$ included signals attributable to a secondary methyl group (0.90 ppm, J=6.9 Hz), four olefinic protons including three mutually coupled olefinic protons (6.21 ppm, dd, J=17.5, 10.7 Hz; 4.94 ppm, br d, J=10.7 Hz; 5.09 ppm, d, J=17.5 Hz and 5.06 ppm, br s), four oxygenated protons (4.09 ppm, dd, J=2.8, 10.9 Hz; 4.19 ppm, m; 4.45 ppm, d, J=12 Hz and 4.50 ppm, br m), and a methylene group adjacent to an imine group (3.85 ppm, dd, J=15.2, 8.8 Hz); 3.68 ppm, m).

Twenty three resonances were observed in the $^{13}$C NMR spectrum of I, including signals attributable to a carbonyl group (204.6 ppm), five olefinic carbons (185.0, 138.8, 135.2, 127.8 and 111.7 ppm), a hemiacetal carbon (109.1 ppm), four oxygenated carbons (83.2, 79.3, 71.6 and 65.6 ppm), and a methylene carbon adjacent to an imine group (54.9 ppm).

DEPT135 and DEPT90 spectra showed the presence of eight methine carbons (including two olefinic and four oxygenated methine carbons), nine methylene carbons (including one olefinic methylene carbon), a methyl group carbon, and by difference from the $^{13}$C NMR spectrum, five quaternary carbons.

The above NMR data together with HSQC revealed the presence of two olefinic double bonds, an imine double bond (the quaternary carbon of which resonated at 185.0 ppm) and a carbonyl group. Therefore the compound I possesses a pentacyclic structure.

The chemical shifts (4.94, 5.09 and 6.21 ppm) and coupling constants (see Table 1) of the mutually coupled olefinic protons and their HSQC correlated

TABLE 1

$^1$H and $^{13}$C NMR data for the compound I designated portimine (*relative to $CD_3OD$ at 49.0 ppm; **relative to $CHD_2OD$ at 3.31 ppm).

| Position | $^{13}$C* | $^1$H (mult, Hz)** |
|---|---|---|
| 1 | 54.9 | 3.68 (m) |
| | | 3.85 (dd, 8.8, 15.2) |
| 2 | 29.4 | 1.92 |
| | | 1.98 |
| 3 | 52.7 | |
| 4 | 185.0 | |
| 5 | 65.6 | 4.50 (m) |
| 6 | 43.1 | 2.10 (dd, 1.7, 15.9) |
| | | 2.80 (dd, 5.2, 15.9) |
| 7 | 109.1 | |
| 8 | 37.6 | 1.67 (dd, 7.4, 12.4) |
| | | 1.99 |
| 9 | 24.6 | 1.72 |
| | | 1.85 |
| 10 | 83.2 | 4.19 (m) |
| 11 | 34.3 | 2.25 (m) |
| 12 | 33.8 | 1.50 (dd, 2.8, 13.9) |
| | | 2.34 (m) |
| 13 | 79.3 | 4.09 (dd, 2.8, 10.9) |
| 14 | 204.6 | |
| 15 | 71.6 | 4.45 (d, 12.0) |
| 16 | 40.7 | 3.70 (br d) |
| 17 | 127.8 | 5.06 (br s) |
| 18 | 135.2 | |
| 19 | 22.6 | 2.34 (2H) |
| 20 | 29.1 | 1.76 (2H) |
| 21 | 138.8 | 6.21 (dd, 10.7, 17.5) |
| 22 | 111.7 | 4.94 (d, 10.7) |
| | | 5.09 (d, 17.5) |
| 231 | 17.6 | 0.90 (d, 6.9) |

$^{13}$C signals (111.7 and 138.8 ppm, respectively) were reminiscent of the chemical shifts of the conjugated exocyclic double bond attached to a six-membered spiro ring, as reported for pinnatoxin G.[1d] The strong UV absorbance with $\lambda_{max}$ 230 nm is consistent with this 1,3-diene.

A combination of HSQC, H2BC and HMBC 2-D data (see Table 2) provided the basic connectivity. The HMBC correlations exhibited by the oxygenated and olefinic protons verified the presence in the compound I of a six-membered spiro-cyclohexene ring with a quaternary spiro-carbon (52.7 ppm, C-3), a CH carbon (40.7 ppm), a protonated olefinic carbon (127.8 ppm), a quaternary olefinic carbon (135.2 ppm), a methylene carbon (22.6 ppm) and another methylene carbon (29.1 ppm) (C-16 to C-20, respectively). The oxygenated proton signals which occurred at 4.50, 4.45 and 4.19 ppm showed HSQC correlations to $^{13}$C NMR signals at 65.6, 71.6 and 83.2 ppm respectively (C-5, C-15, C-10), while the oxygenated proton signal which occurred at 4.50 ppm exhibited an HMBC correlation to the quaternary hemiacetal carbon at 109.1 ppm (C-7), as did three of the four protons attached to methylene groups which occurred at 24.6 and 37.6 ppm (C-9 and C-8). The secondary CH(Me) methine proton at 2.25 ppm showed correlations to one of the foregoing methylene carbons (C-9), another methylene carbon (33.8 ppm, C-12), two oxygenated carbons (79.3 and 83.2 ppm, C-13 and C-10) and the secondary methyl group carbon (17.6 ppm, C-23).

H2BC correlations, in combination with HSQC data, showed that the oxygenated carbons with shifts at 65.6, 83.2 and 79.3 ppm (C-5, C-10 and C-13) were adjacent to methylene carbons which occurred at 43.1, 24.6 and 33.8 ppm (C-6, C-9 and C-12), while the oxygenated carbon which occurred at 71.6 ppm (C-15) was located adjacent to the methine carbon at 40.7 ppm (C-16). HMBC correlations observed for the H-11 (2.25 ppm), H-12a (1.50 ppm) and H-12b (2.34 ppm) (see Table 2), in combination with TOCSY data which traced out the H-8 to H-13 spin system, defined the location of the C-10 (83.2 ppm) ether carbon.

A detailed analysis of all this 2D-NMR data in combination with $^1$H-$^1$H correlations observed in COSY and TOCSY spectra established the primary structure for the compound I. This analysis showed that the compound I was a polycyclic ether and possessed a five-membered imine ring rather than the seven-membered imine ring that characterises pinnatoxin G and related analogues from *V. rugosum*.

TABLE 2

H2BC and HMBC correlations (δ ppm in CD$_3$OD) observed for the compound I ([a]Signal assignments appear in Table 1, [b]Coupling constants and signal multiplicities are given in Table 1, [c]Low intensity correlations are bracketed).

| $^1$H signal[b] | Correlated $^{13}$C signals[a] | |
| --- | --- | --- |
| | H2BC | HMBC |
| 1    3.68 | 29.4 | 29.4, (65.6)[c], 185.0 |
|      3.85 | 29.4 | 29.4, 52.7, 185.0 |
| 2    1.92 | 54.9 | 185.0 |
|      1.98 | 54.9 | 185.0 |
| 5    4.50 | 43.1 | 43.1, (109.1), 185.0 |
| 6    2.10 | 65.6 | 37.6, 40.7), 65.6, 109.1, 185.0 |
|      2.80 | 65.6 | 37.6, (40.7), 109.1 |
| 8    1.67 | 24.6 | 109.1 |
|      1.99 | 24.6 | 109.1 |
| 9    1.72 | 37.6 | 109.1 |
|      1.85 | 37.6 | |
| 10   4.19 | 24.6 | 34.3, 1091 |
| 11   2.25 | 83.2, 33.8, 17.6 | 17.6, 24.6, 33.8, 79.3, 83.2 |
| 12   1.50 | 34.3, 79.3 | 17.6, 34.3, 79.3, 83.2, 204.6 |
|      2.34 | 34.3, 79.3 | 34.3, 79.3, 83.2, 204.6 |
| 13   4.09 | 33.8 | 33.8, 34.3, (40.7), 71.6 |
| 15   4.45 | 40.7 | 40.7, 109.1, 127.8, 204.6 |
| 16   3.70 | 71.6 | |
| 17   5.06 | 40.7 | 22.6, 40.7, 52.7, 71.6 |
| 19   2.34 (2H) | 29.1 | |
| 20   2.91 (2H) | 22.6 | 22.6, 135.2, 185.0 |
| 21   6.21 | 111.7 | 22.6, 127.6, 135.2 |
| 22   4.94 | 138.8 | 135.2, 138.8 |
|      5.09 | 138.8 | 127.8, 135.2, 138.8 |
| 23   0.90 | 34.3 | 33.8, 34.3, (79.3), 83.2 |

The C-16 stereochemistry of the compound I is likely to be the same as that for the equivalent carbon in the cyclohexene ring in the pinnatoxins. Based on this assumption, NOESY and ROESY data defined the relative stereochemistry of the other chiral centres of the compound I relative to that assumed for H-16. Structurally significant NOE's are presented in FIG. 1.

A crucial aspect of the stereochemical determination required distinguishing NOESY or ROESY enhancements arising for three of the four C-12 and C-19 methylene proton signals which exhibited partially or fully overlapped resonances in the 2.3-2.4 ppm region of the $^1$H NMR spectrum. Since the $^{13}$C NMR shifts of this pair of methylene groups differ (33.8 and 22.6 ppm, respectively), HSQC-NOESY and HSQC-ROESY spectral data were used to define the interactions of the respective C-12 and C-19 protons. These spectra established that the pair of methylene protons attached to C-19 showed NOESY correlations to the pair of H-20 methylene protons which occurred at 1.76 ppm and to the olefinic proton (H-22b) which occurred at 5.09 ppm, while the C-12 methylene proton that also resonated at 2.34 ppm exhibited correlations to one of the C-9 methylene protons (1.85 ppm) and the oxygenated C-15 methine proton (4.45 ppm) (FIG. 1).

All possible stereoisomeric configurations of the five asymmetric carbon atoms in the C-7 to C-15 portion of the portimine structure were modeled (Chem3D) relative to that assumed for C-16. Only the compound I was found to be consistent with the above HSQC resolved NOESY correlations. The collision induced fragmentation mass spectrum for the [M+H]+ ion was consistent with the compound I and can be rationalised as proceeding mainly via an intramolecular retro-Diels-Alder ring-opening. A similar ring opening has been proposed for other cyclic imines (Sleno et al (2004)).

Analytical Standard

Monitoring the occurrence in the environment or harvested marine organisms of potentially toxic secondary metabolites requires the availability of analytical standards. In the absence of such standards it is not possible to perform quantitative analyses on samples obtained from disparate sources or make reliable comparisons between analyses performed in different laboratories, at different locations, or by different operators. The prominent fragment ions at m/z 134.1 and 148.1 are useful for sensitive LC-MS/MS (MRM) monitoring for the presence of portimine in cultures and other extracts. An SPE extract of seawater from a tidal bay in which *V. rugosum* was a prominent component of the benthic microalgae gave readily detectable levels of the compound I, pinnatoxin-E and pinnatoxin-F. However, flesh of Pacific oysters from this area containing 20-200 µg/Kg of pinnatoxins (McNabb et al (2012)) did not contain detectable levels of the compound I (<0.1 µg/Kg).

Biological Activity

Figure 2:
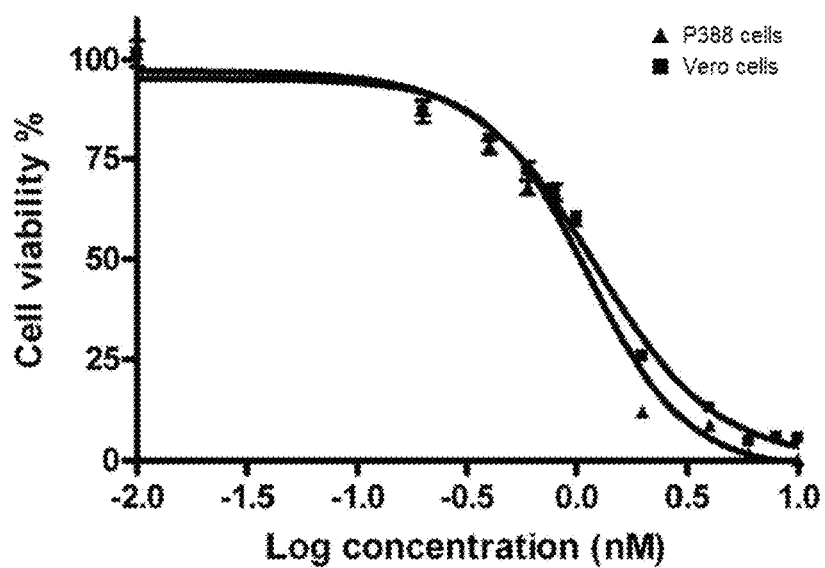
FIG. 2. Dose response curves for the compound I designated portimine against P388 (▲) and Vero (■) cells over 72 hours exposure.

The $LD_{50}$ of the compound I in mice by intraperitoneal injection was 1570 µg/kg (95% CI 1269 to 3080 µg/kg). No effects were recorded at 500 or 700 µg/kg. The acute toxicity of the compound I to mice by this route of administration is thus much lower than that reported for many other cyclic imines, such as desmethyl spirolide C ($LD_{50}$ 6.9 µg/kg), gymnodimine ($LD_{50}$ 96 µg/kg) and pinnatoxin F ($LD_{50}$ 16 µg/kg). Furthermore, the onset of symptoms of toxicity was much slower with the compound I than with other cyclic imines. Structure-activity relationships among cyclic imines, both in terms of acute toxicity and effects on neuromuscular transmission, point to the importance of the imine moiety in the mode of action (Munday (2008)). The presence of the imine moiety is not a sufficient condition for toxicity, however, as seen with the compound I and with spirolide H, which is even less toxic to mice than the compound I (Roach et al (2009)). The in vitro dose-response curves against two mammalian cell types showed that the compound I was highly toxic with >90% cells killed at 10 nM after 72 hours of exposure (FIG. 2) (Shi (2012)). The $EC_{50}$ values were 2.7 nM and 3.0 nM for P388 and Vero cells, respectively. Activation of caspase-3, a critical apoptosis indicator, was observed in P388 cells after 12 hours of exposure suggesting that the compound I is an apoptosis inducer (Shi (2012)). Although the compound I was very much less toxic to mice than pinnatoxin-F, it was much more toxic to P388 cells in vitro ($EC_{50}$ 2.7 nM versus >1 µM). This toxicity profile prompted further investigations into the use of the compound I as an anticancer therapeutic or synergist for Bcl-2 antagonists such as the compound designated ABT-737:

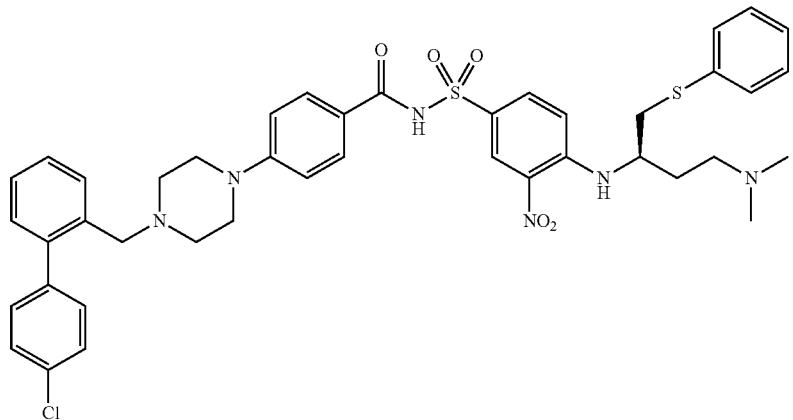

ABT-737

The compound ABT-737 is one of a number of antagonists of antiapoptotic (prosurvival) proteins developed for use in the treatment of neoplasia, including the lymphoid malignancies chronic lymphocytic leukaemia (CLL) and pediatric acute lymphoblastic leukaemia (ALL). The structures off other compounds belonging to this class of drugs, generally referred to as "BH3 mimetics" and demonstrated to have in vivo efficacy in preclinical models or clinical trials (Billard (2013)) are presented on the following page. More recently, discovered members of this class of drugs that are potent Mcl-1/Bcl-xl dual inhibitors are described elsewhere (e.g. Tanaka et al (2013)).

Use of the Compound I as a Therapeutic

Cytotoxic compounds typically activate the intrinsic apoptosis pathway in cells by damaging DNA, proteins or lipids. At high concentrations this damage can directly compromise the metabolic status and membrane integrity of cells, leading to direct necrotic cell death. With many cytotoxic compounds the "apoptotic window" can be small, and a mixture of apoptotic and necrotic death ensues (Hampton and Orrenius (1997)). The mechanisms of

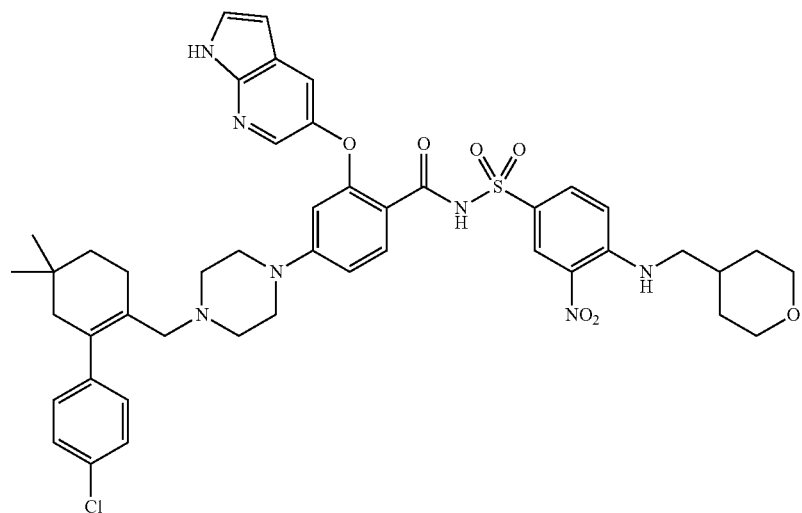

ABT-199

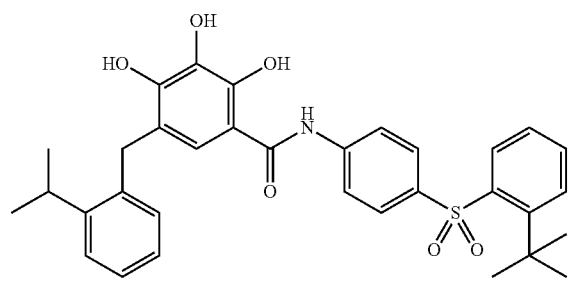

TW-37

-continued
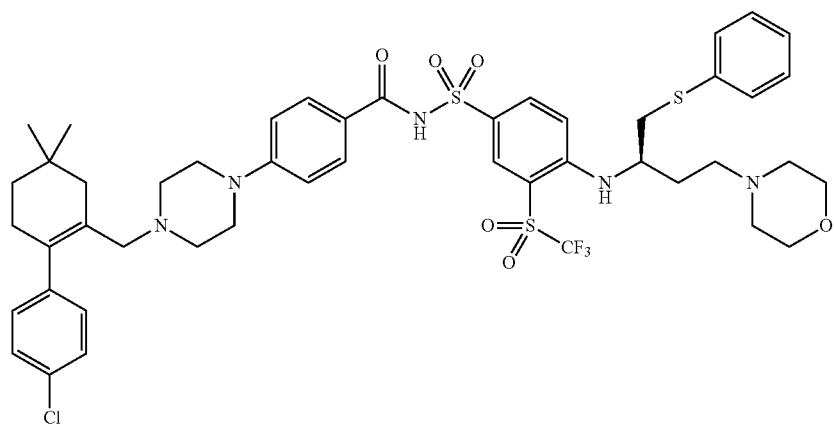
ABT-263 (navitoclax)
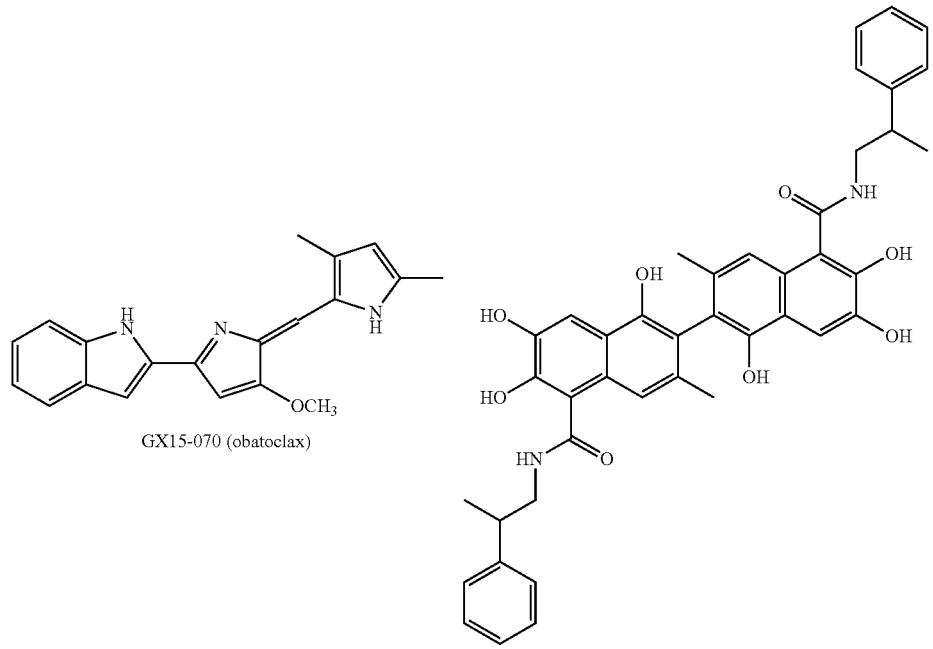
GX15-070 (obatoclax)
BI97CI (sabutoclax)
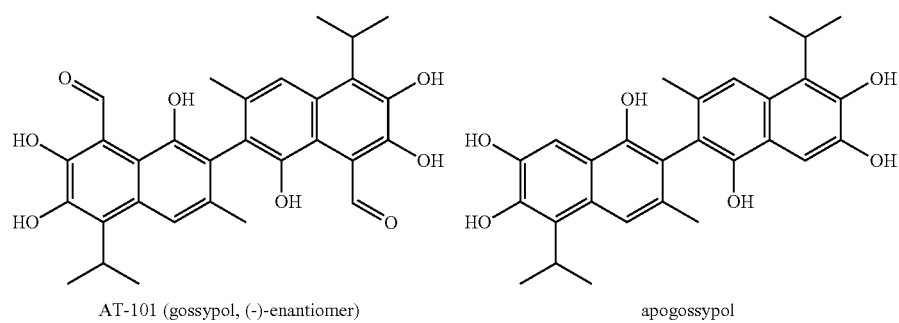
AT-101 (gossypol, (-)-enantiomer)
apogossypol -continued

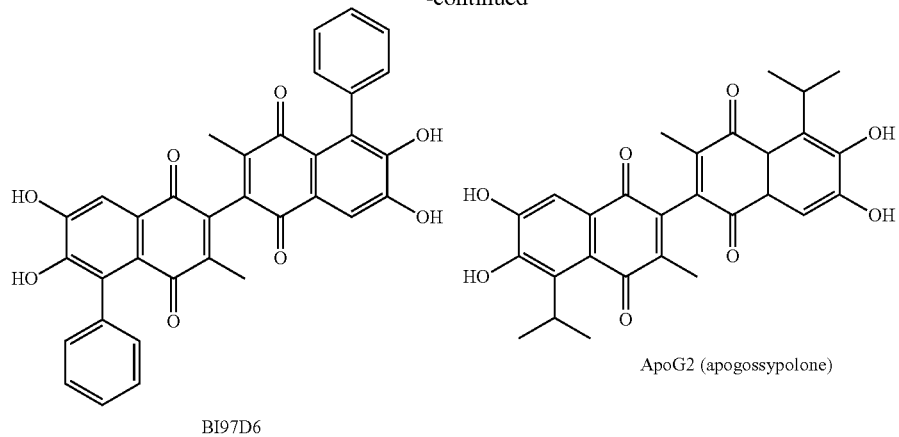

BI97D6

ApoG2 (apogossypolone)

portimine cytotoxicity were investigated by assessing the mode of cell death in human T-lymphoma cells, and determining the effect of overexpressing Bcl-2, an endogenous inhibitor of intrinsic apoptosis (Chipuk et al (2010)). Surprisingly, the results show that portimine is an exclusive apoptosis inducer, with no cell death occurring in Bcl-2 overexpressing cells even at high doses. A combination treatment of portimine and the Bcl-2 inhibitor ABT-737 resulted in strong induction of apoptosis in selection of transformed haematological cell lines.

Materials and Methods

RPMI 1640 [+] L-Glutamine, Iscoves DMEM, fetal bovine serum (FBS), penicillin/streptomycin and Annexin V-FITC were obtained from Gibco-BRL (Invitrogen, Auckland, New Zealand). Propidium iodide and DMSO were obtained from Sigma-Aldrich (St Louis, Mo., USA). DEVD-AMC was obtained from the Peptide Institute (Catalog#3171-v). ABT-737 was the gift of Dr David Huang (WEHI, Melbourne, Australia). Pinnatoxin F and pinnatoxin G were purified as previously described.

Cell Culture and Treatment

Jurkat T-lymphocyte-like, pro-myelocytic HL60 and erythroleukemic K562 cell lines were obtained from the American Type Culture Collection (ATCC, Rockville, Md., USA). The B9 Jurkat cell clone that overexpresses Bcl-2 was previously generated and characterised (Thomson et al (2005)). Jurkat and HL60 cells were grown in culture using RPMI 1640 media supplemented with 10% FBS, 100 units/mL penicillin and 100 µg/mL streptomycin at 37° C. in a humidified atmosphere with 5% $CO_2$. K562 cells were grown in culture using Iscoves DMEM media supplemented with 10% FBS, 100 units/mL penicillin and 100 µg/mL streptomycin at 37° C. in a humidified atmosphere with 5% $CO_2$.

All cells were treated at $1\times10^6$ per mL in media. Fresh stock solutions of ABT-737 were prepared in sterile DMSO and stored at −20° C. Stock solutions of 50 mM were then further diluted with DMSO and added to cells, maintaining the final concentration of DMSO constant at 0.1%. Jurkat and K562 cells were treated with 200 nM ABT-737, HL60 cells were treated with 50 nM ABT-737. Stocks of the compound I, pinnatoxin F and pinnatoxin G (1000×) were prepared in sterile DMSO and stored at −20° C. Concentrations were calculated using molecular weights of 401 (the compound I), 764 (pinnatoxin F) and 693 (pinnatoxin G). The final concentration of DMSO was kept constant at 0.1%.

Viability Assay

Integrity of cell plasma membranes was assessed using propidium iodide (PI) staining at 48 hours. Cells ($0.2\times10^6$) were loaded with 1 µg of propidium iodide (1 µL of a 1 mg/mL stock in water per 200 µL of cells). PI uptake by non-viable (stained, PI positive) cells was measured using the FC500 MPL Flow Cytometry system (Beckman Coulter Inc.). Viable cells were defined as PI-negative cells expressed as a percentage of the 10,000 cells analysed.

Phosphatidylserine Assay

Phosphatidylserine (PS) becomes exposed on the outer leaflet of the plasma membrane during apoptosis. PS binds strongly with Annexin-V, which when labeled with a fluorescent probe such as fluorescein isothiocyanate (FITC), allows the detection of cells undergoing apoptosis. Treated cells ($0.1\times10^6$) were harvested and centrifuged at 10,000×g for 1 minute. The supernatant was removed and cells were resuspended in 100 µL Annexin-V Binding Buffer (10 mM HEPES pH 7.4, 140 mM NaCl, 2.5 mM $CaCl_2$). Cells were stained by adding 1 µL Annexin-V FITC conjugate, and then incubated in the dark at room temperature for 15 minutes. A further 150 µL 1×Binding Buffer containing 5 µL of propidium iodide (1 mg/mL stock) was added to the solution before analysis by flow cytometry using the FC500 MPL Flow Cytometry system (Beckman Coulter Inc.). Viable cells (PI negative) that stained with Annexin-V FITC were termed PS positive.

Caspase Assay

Six hours after treatment $1\times10^6$ cells were harvested and stored as cell pellets at −80° C. Cell pellets were resuspended in 15 µL PBS, transferred to a 96-well fluorescent plate, and 95 µL buffer (100 mM HEPES, 10% sucrose, 5 mM DTT, 0.1% NP-40 and 0.1% CHAPS at pH 7.25) containing 50 µM DEVD-AMC. The rate of release of fluorescent AMC was monitored at 37° C. ($\lambda_{ex}$ 390 nm, $\lambda_{em}$ 460 nm). Data are expressed as a fold increase in activity over vehicle-treated cells incubated for the same time.

Statistics

The means and standard errors of n (stated in the Brief Description of Drawings) independent experiments were plotted with the SigmaPlot software package (SPSS Science, Chicago, Ill.) and statistical analysis undertaken. Unless stated otherwise, analysis of variance (ANOVA) was used, followed by the Bonferroni test for multiple comparisons. The differences were considered statistically significant when the p-value was <0.05.

Results

Figure 3A:
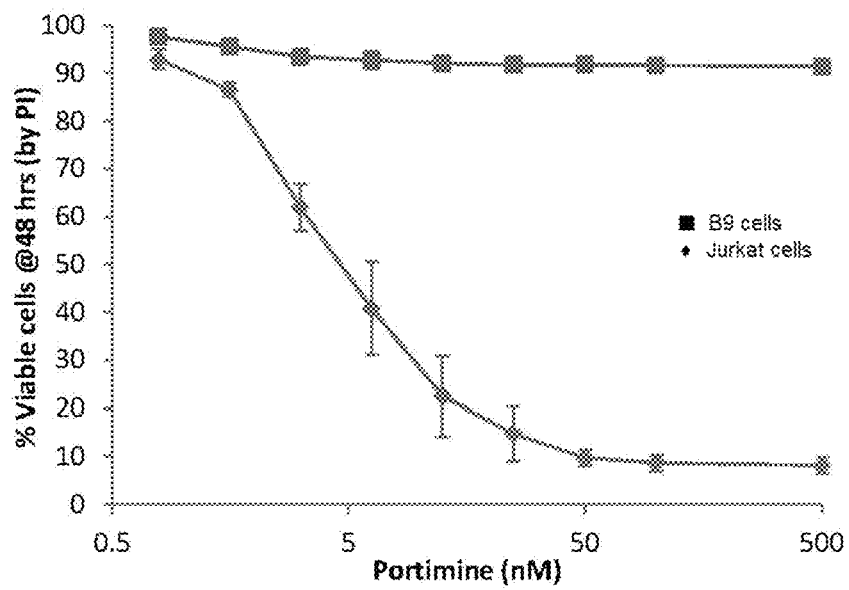
FIG. 3. Viability (A) and caspase activity (B) of cells (■, B9; ♦, Jurkat) following exposure to increasing concentration of the compound I.
Figure 3B:
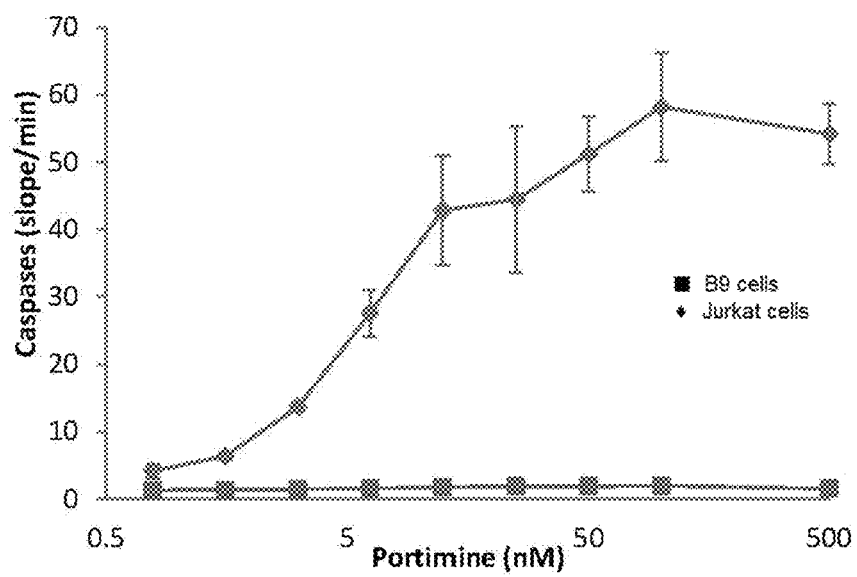
Figure 4:
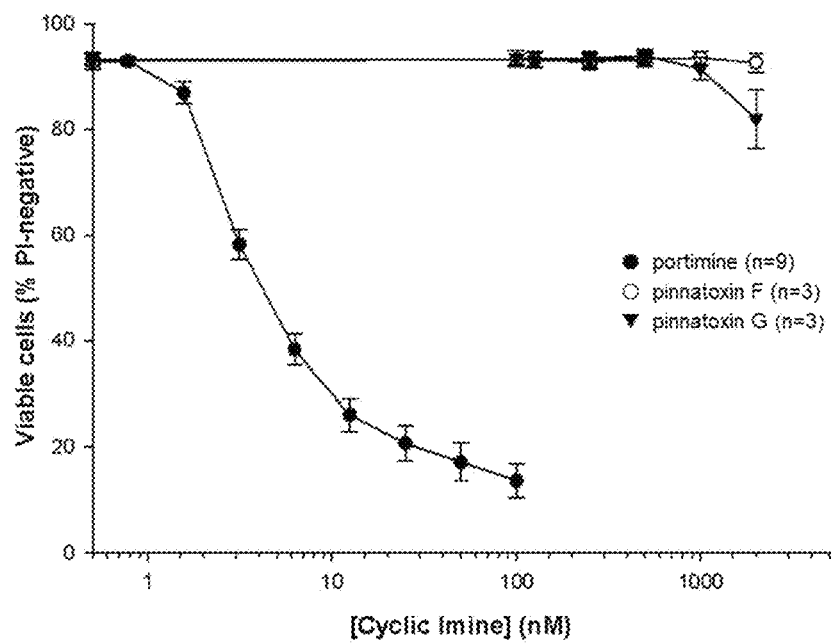
FIG. 4. Jurkat cells ($1 \times 10^{6}$/mL) were incubated in media with increasing concentrations of portimine (•, n=9), pinnatoxin F (○, n=3) or pinnatoxin G (▼, n=3) for 48 hours before cell viability was measured.
Figure 5:
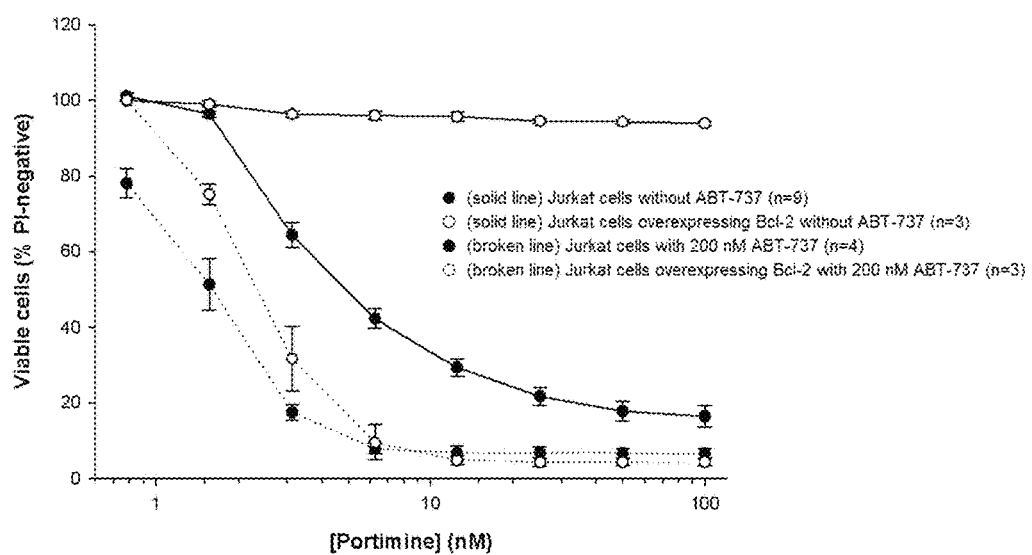
FIG. 5. Wild-type or Bcl-2 overexpressing Jurkat cells ($1 \times 10^{6}$/mL) were incubated with increasing concentrations of portimine in the presence or absence of 200 nM ABT-737 for 48 hours before cell viability was measured (Jurkat without ABT-737 (•, solid line; n=9); Jurkat overexpressing Bcl-2 without ABT-737 (○, solid line; n=3); Jurkat with 200 nM ABT-737 (s, broken line; n=4); Jurkat overexpressing Bcl-2 with 200 nM ABT-737 (•, broken line; n=3).

Jurkat T-lymphoma cells in media were exposed to a range of concentrations of portimine before cell viability was assessed using propidium iodide staining by flow cytometry. The compound I was highly cytotoxic, with an $LC_{50}$ of 6.0 nM (FIG. 3). In contrast, two related cyclic imines, pinnatoxin F and pinnatoxin G, displayed little cytotoxicity over the concentration range tested (FIG. 3). The anti-apoptotic protein Bcl-2 is frequently overexpressed in cancer cells where it conveys a survival advantage against pro-apoptotic stimuli (Chipuk et al (2010)). The compound I was unable to trigger cell death in cells overexpressing Bcl-2, even at the highest concentrations tested (FIG. 4). However, the BH3 mimetic ABT-737, which blocks the anti-apoptotic effect of Bcl-2 (Olterdorf et al (2005)), but is not directly cytotoxic at 200 nM, rendered the cells sensitive to the compound I ($LC_{50}$=2.4 nM). ABT-737 also sensitized wild-type Jurkat cells to portimine, lowering the $LC_{50}$ to 1.4 nM.

Figure 6A:
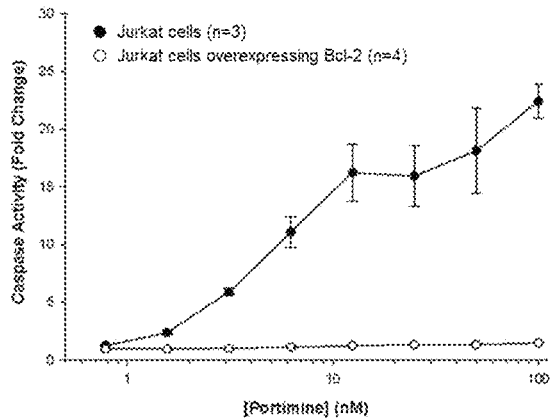
FIG. 6. Wild-type or Bcl-2 overexpressing Jurkat cells ($1 \times 10^{6}$/mL) were incubated with increasing concentrations of portimine in the presence or absence of 200 nM ABT-737. (A) Cells were harvested 6 hours after treatment and caspase activity was measured (Jurkat cells (•, n=3); Jurkat cells overexpressing Bcl-2 (○, n=4)). (B) Cells were harvested at selected times following treatment with 50 nM portimine (Jurkat cells (•, n=7); Jurkat cells overexpressing Bcl-2 (○, n=7)). (C) Cells were treated with 50 nM portimine in the presence or absence of 200 nM ABT-737 for selected times (Jurkat cells (•, n=7); Jurkat cells plus 200 nM ABT-737 (○, n=3); Jurkat cells overexpressing Bcl-2 (▼, n=7); Jurkat cells overexpressing Bcl-2 plus 200 nM ABT-737 (Δ, n=4)).
Figure 6B:
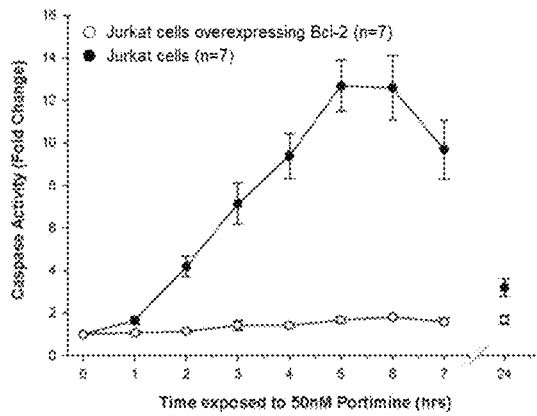
Figure 6C:
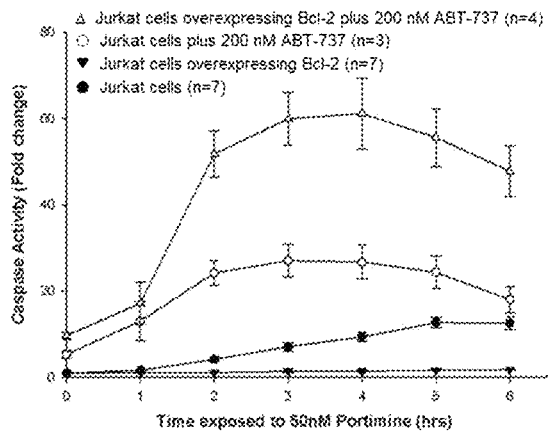

Caspase-3-like DEVDase activity was measured in wild-type and Bcl-2 overexpressing Jurkat cells treated with increasing concentrations of the compound I. There was a dose-dependent increase in caspase activation in wild-type cells, but no caspase activity was measured at any concentration in the Bcl-2 overexpressing cells (FIG. 6A). Time course experiments indicated a steady increase in caspase activity over the 5 hours following portimine exposure, then a decrease at later times, consistent with a loss in cell viability (FIG. 6B). ABT-737 in combination with the compound I resulted in a dramatic increase in caspase activation, particularly in the Bcl-2 overexpressing cells, with a 60-fold increase in caspase activity (FIG. 6C).

Figure 7:
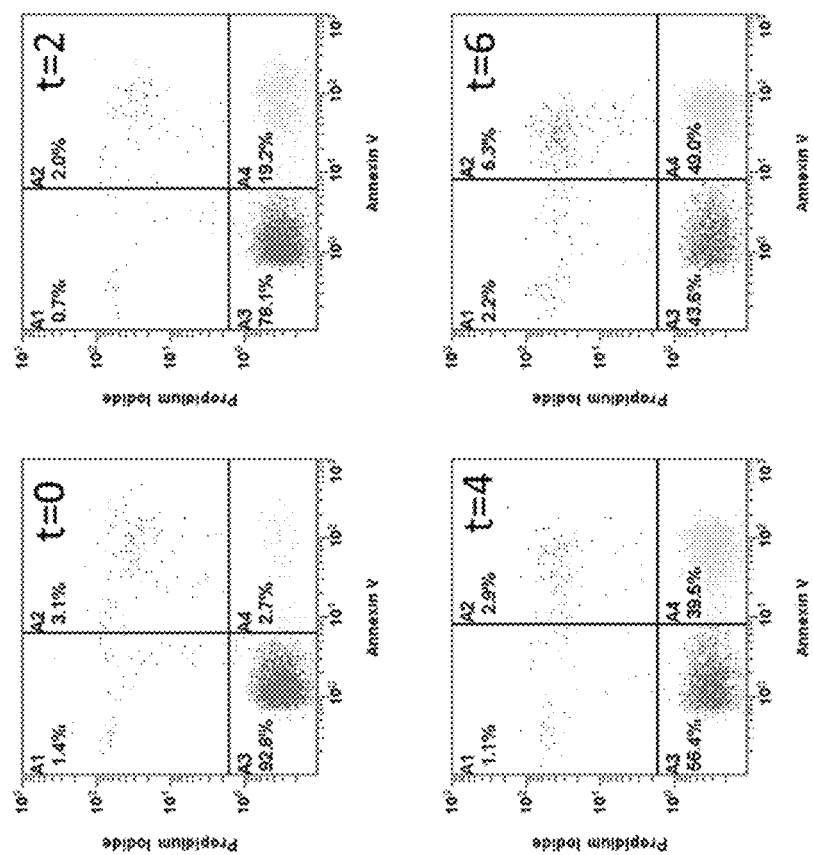
FIG. 7. Jurkat cells ($1 \times 10^{6}$/mL) were treated with 50 nM portimine for selected times before staining for phosphatidylserine (Annexin V) and viability (propidium iodide). Raw data from a representative experiment is shown, with necrotic cells in quadrants A1 and A2, normal cells in A3, and apoptotic cells in A4.
Figure 8A:
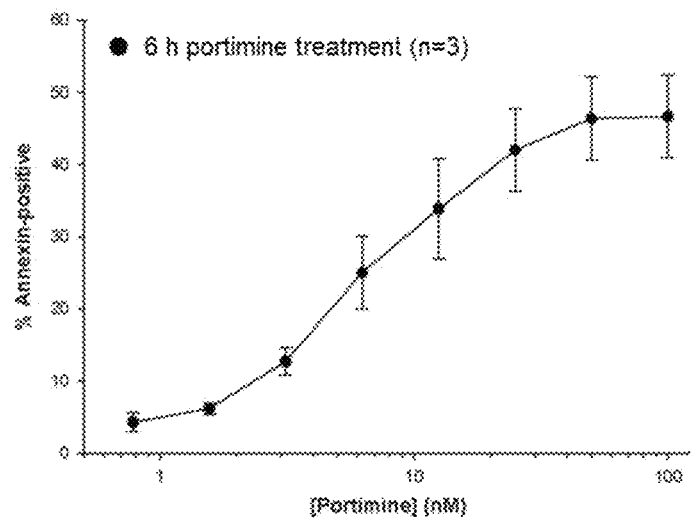
FIG. 8 Dose-response plotting the number of apoptotic cells after 6 h portimine treatment (n=3)(A) and time course plotting the number of apoptotic cells following treatment with 50 nM portimine (n=3)(B).
Figure 8B:
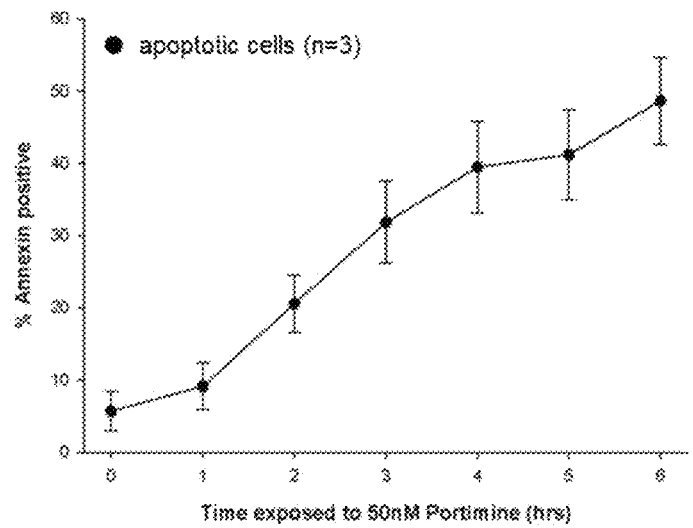

The induction of apoptosis was also quantified by flow cytometry measurement of annexin V-FITC labeling of individual cells. Annexin V binds to cells in which phosphatidylserine has been externalized to the outer leaflet of the plasma membrane, with early stage apoptotic cells becoming annexin V-positive but remaining propidium iodide-negative. Cells that are positive for both annexin V and propidium iodide are necrotic, but it is not possible to determine if their mode of death was necrosis or as a result of secondary apoptosis, i.e. an eventual loss of membrane integrity after completion of the apoptotic program. Portimine proved to be an excellent trigger of phosphatidylserine exposure, with positive cells evident at 2 hours, and up to 50% of the cells being annexin V positive at 6 hours, yet there was no indication of significant necrosis (FIGS. 7, 8A and 8B).

Figure 9:
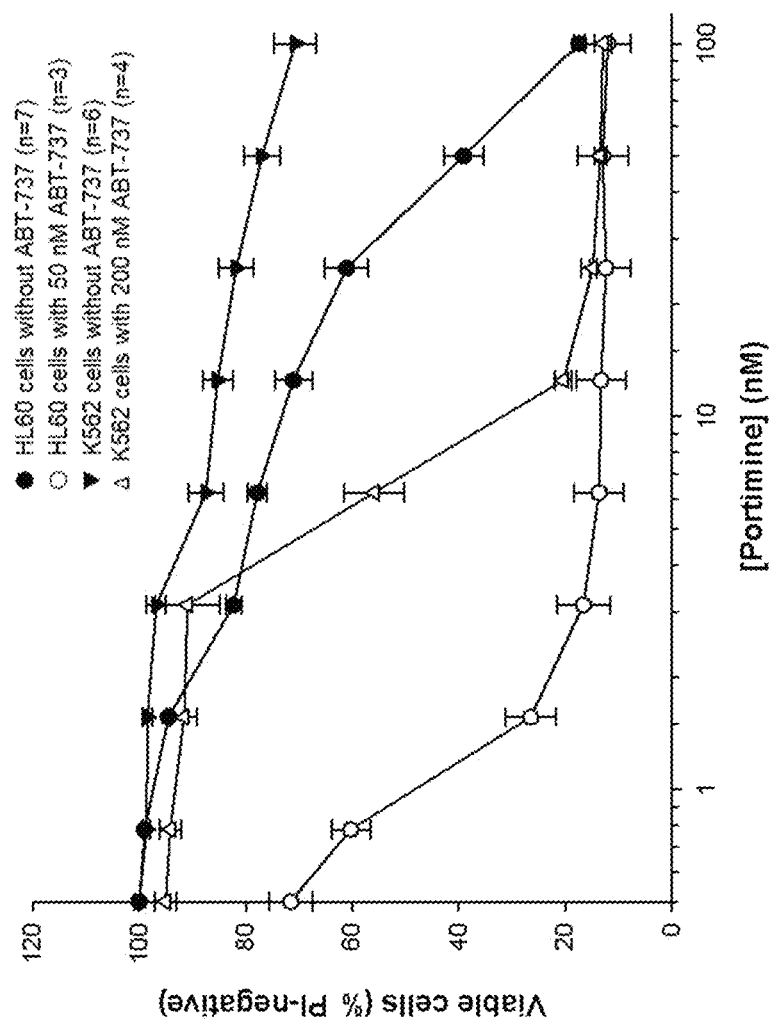
FIG. 9. HL60 or K562 cells were incubated ($1 \times 10^{6}$/mL) with increasing concentrations of portimine in the presence or absence of ABT-737 for 48 h before cell viability was measured (HL60 cells without ABT-737 (•, n=7); HL60 cells with 50 nM ABT-737 (o, n=3); K562 cells without ABT-737 (▼, n=6); K562 cells with 200 nM ABT-737 (Δ, n=4)).

The compound I was tested against the pro-myelocytic cell line HL60 and the multi-drug resistant myelogenous leukemia cell line K562 (FIG. 9). HL60 cells were relatively more resistant to the compound I than the Jurkat cells ($LC_{50}$=34 nM), but they were particularly sensitive to ABT-737. The ABT-737 was therefore lowered to 50 nM to look for synergistic effects with the compound I. Under these conditions the compound I had an $LC_{50}$ of 0.8 nM. The K562 cells were also relatively resistant to the compound I, but ABT-737 was able to lower the $LC_{50}$ to 6.7 nM.

The compound I is a potent inducer of cell death in a selection of haematological cell lines, and its mode of cell death appears almost exclusively to be via the induction of apoptosis. The compound I is active at low nanomolar (nM) concentrations, which is considerably lower than the concentrations at which many other small molecule apoptosis-inducers are active. In addition, other cytotoxic compounds typically induce damage to cellular macromolecules, and at higher concentrations this damage triggers necrosis regardless of increased expression of endogenous anti-apoptotic proteins or the removal of essential apoptotic machinery. The effects of the compound I are more concordant with the action of pro-apoptotic ligands such as Fas, TNF and TRAIL, which are strong inducers of apoptosis at low concentration and do not cause cellular damage or unregulated necrosis at higher doses. Regardless of the mechanism of action, the compound I has favourable attributes as a chemical inducer of apoptosis. Of particular note is the clear population of phosphatidyl-serine positive/propidium iodide negative cells, with up to 50% of the cells in a population of cells exposed to the compound I present in this quadrant. The in vitro ability of the anti-apoptotic protein Bcl-2 to completely prevent cell death triggered by the compound I may indicate that the compound I would be ineffective when used alone in the treatment of subjects with neoplasia.

There are five recognized anti-apoptotic members of the Bcl-2 family, which in addition to Bcl-2 includes Bcl-XL, Bcl-w, Mcl-1 and A1. Overexpression of these proteins is associated with tumour development and resistance to therapy (Chipuk et al (2010); Letai et al (2004)). ABT-737 was the first of a class of drugs designed to antagonize the action of Bcl-2 family members (Ottersdorf et al (2005)), but does not effectively target all of these proteins. Relapses of initially positive responses have been associated with increased expression of Mcl-1 (van Delft et al (2006)).

Use of the Compound I as a Lead Compound

Drug discovery efforts are focused on new antagonists, or combinations of antagonists, that can target all Bcl-2 family members. It is anticipated that the compound I will be susceptible to structural modification to provide congeners retaining the biological activity of the parent compound, but having optimised pharmacodynamic and pharmacokinetic properties. It is further anticipated that these congeners may be provided via modification of the hydroxyl groups located at carbons 5 and 13, modification of the carbonyl group located at carbon 14, and/or modification of the double bonds located between carbons 17 and 18 and carbons 21 and 23. These structural modifications may include substitution, saturation and/or epoxidation by methods known in the art of medicinal chemistry. Examples of such modifications of the hydroxyl groups include the formation of ether bonds by reaction with an epoxide or oxirane group, formation of an ester bond by reaction with an acid halide (e.g. an acid chloride), formation of a carbamate linkage via an imidazole or a succinimidyl carbamate intermediate and/or formation of a carbamate linkage via an isocyanate intermediate. Examples of such modifications of the carbonyl (ketone) group include the formation of a hydrazone linkage by reaction with a hydrazide compound, formation of a Schiff base by reaction with a primary or secondary amine (with our without subsequent reduction to a secondary amine) and/or participation of the carbonyl function in a Mannich type condensation reaction. Examples of such modifications of the double bonds, in particular the double bond located between carbons 21 and 22, include hydrogenation, halogenation, hydration and/or oxidation. The susceptibility of the internal ethers (between carbons 7 and 10 and 7 and 15) modification should be considered.

Although the invention has been described with reference to embodiments or examples it should be appreciated that variations and modifications may be made to these embodiments or examples without departing from the scope of the invention. Where known equivalents exist to specific elements, features or integers, such equivalents are incorporated as if specifically referred to in this specification. In particular, variations and modifications to the embodiments or examples that include elements, features or integers disclosed in and selected from the referenced publications are within the scope of the invention unless specifically disclaimed. The advantages provided by the invention and discussed in the description may be provided in the alternative or in combination in these different embodiments of the invention.

REFERENCED PUBLICATIONS

Billard (2013) BH3 Mimetics: Status of the Field and New Developments Mol Cancer Ther 12(9), 1691-1700

Cembella and Krock (2008) In *Seafood and Freshwater Toxins: pharmacology, physiology and detection*; Botana, L. M., Ed.; CRC Press: Boca Raton, Fla.; pp 561-580

Chipuk et al (2010) *The BCL-2 family reunion* Molecular Cell, 37(3), 299-310

Feher and Schmidt (2003) J. Chem. Inf. Comput. Sci., 43, 218-227

Fuchs and Steller (2011) *Programmed Cell Death in Animal Development and Disease* Cell, 147, 742-758

Hampton and Orrenius (1997) *Dual regulation of caspase activity by hydrogen peroxide: implications for apoptosis* FEBS letters, 414(3), 552-6

Hampton and Orrenius (1997) *Dual regulation of caspase activity by hydrogen peroxide: Implications for apoptosis* FEBS Letters, 414(3), 552-6

Hellyer et al (2011) Toxicon., 58, 693-699

Hu et al (1995) J. Chem. Soc., Chem. Commun. 1995, 2159-2161

Kharrat et al (2008) *The marine phycotoxin gymnodimine targets muscular and neuronal nicotinic acetylcholine receptor subtypes with high affinity* Journal of Neurochemistry, 107(4), 952-63

Kita and Uemura (2005) Chemistry Letters, 34, 454-459

Kita et al (2005) Bioorganic & Medicinal Chemistry, 13, 5253-5258

Letai et al (2004) *Antiapoptotic BCL-2 is required for maintenance of a model leukemia* Cancer Cell, 6(3), 241-9

Lu et al (2001) Tetrahedron Lett., 42, 1713-1716

McCarron et al (2012) J. Agric. Food Chem. 2012, 60, 1437-1446

McNabb et al (2012) Harmful Algae, 13, 34-39

Molinski et al (2009) Nature reviews-Drug discovery, 8, 69-85

Munday (2008) In *Seafood and Freshwater Toxins: pharmacology, physiology and detection*; Botana, L. M., Ed.; CRC Press: Boca Raton, Fla.; pp 581-594

Munday et al (2012) Acute toxicity of pinnatoxins E, F and G to mice. Toxicon: Official journal of the International Society on Toxicology, 60(6), 995-9

Nézan and Chomérat (2010) Cryptogam. Algol., 32, 3-18

Oltersdorf et al (2005) *An inhibitor of Bcl-2 family proteins induces regression of solid tumours* Nature, 435(7042), 677-81

Oltersdorf et al (2005) *An inhibitor of Bcl-2 family proteins induces regression of solid tumours* Nature, 435(7042), 677-681

Rhodes et al (2011) Phycologia, 50, 624-628;

Roach et al (2009) J. Nat. Prod., 72, 1237-1240

Seki et al (1995) Tetrahedron Lett., 36, 7093-7096

Selwood et al (2010) J. Agric. Food Chem. 2010, 58, 6532-6542

Selwood et al (2013) *Portimine: a bioactive metabolite from the benthic dinoflagellate Vulcanodinium rugosum* Tetrahedron Letters, 54(35), 4705-4707

Shi (2012) *Chemical and toxicological investigation of the toxic dinoflagellate, Karenia brevisulcata.* Doctoral (Ph.D.) thesis, Lincoln University, Christchurch, 2012. http://hdl.handle.net/10182/4547

Steno et al (2004) Anal. Bioanal. Chem. 2004, 378, 969-976

Takada et al (2001) Tetrahedron Lett. 2001, 42, 3495-3497

Tanaka et al (2013) *Discovery of potent Mcl-1/Bcl-xl dual inhibitors by using a hydribization strategy based on structural analysis of target proteins* J. Medicinal Chem., 56, 9635-9645.

Thomson et al (2006) *Phenethyl isothiocyanate triggers apoptosis in Jurkat cells made resistant by the overexpression of Bcl-2* Cancer Research, 66, 6772-6777

Torigoe et al (1988) J. Am. Chem. Soc., 110, 7876-7877

Uemura et al (1995) J. Am. Chem. Soc. 1995, 117, 1155-1156 van Delft et al (2006) *The BHC mimetic ABT-737 target selective Bcl-2 proteins and efficiently induces apoptosis via Bak/Bax if Mcl-1 is neutralised* Cancer Cell, 10(5), 389-399 van Wagoner et al (2011) Tetrahedron Lett. 52 (33), 4243-4246

Zhou et al (2012) *Structure-based design of potent Bcl-2/Bcl-xL inhibitors with strong in vivo antitumor activity* J. Medicinal Chem., 22, 6149-6161.

The invention claimed is:

1. A congener of portimine of the structure:

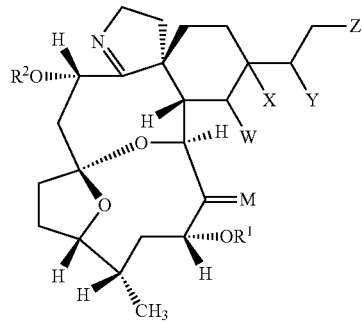

where: $R^1$ is selected from the group consisting of: H, acyl, alkyl, alkylene, aryl and aralkyl; $R^2$ is selected from the group consisting of: H, acyl, alkyl, alkylene, aryl and aralkyl; M is O, S, N—$NH_2$, N(alkyl)$_2$, N-alkoxy or N(aryl)$_2$; W and X may form a bond, an epoxide, or are independently selected from the group consisting of: H, halogen, OH and O-acyl; Y and Z form a bond, an epoxide, or are independently selected from the group consisting of: H, halogen, OH and O-acyl; and when $R^1$ and $R^2$ are H, then M is not O, or W and X or Y and Z do not form a bond.

2. The congener of claim 1 where $R^1$ and $R^2$ are unsubstituted.

3. A congener of portimine of the structure:

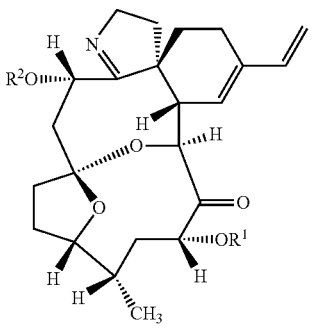

where R¹ is selected from the group consisting of: H, acyl, alkyl, alkylene, aryl and aralkyl; R² is selected from the group consisting of: H, acyl, alkyl, alkylene, aryl and aralkyl; and both R¹ and R² are not H.

4. The congener of claim 3 where R¹ and R² are unsubstituted.

5. A congener of portimine of the structure:

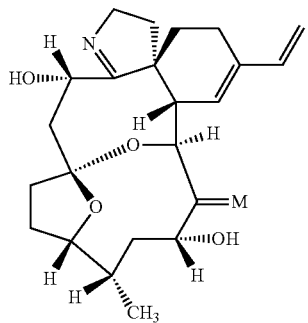

where M is S, N—NH₂, N(alkyl)₂, N-alkoxy or N(aryl)₂.

6. The congener of claim 5 where the alkyl, alkoxy or aryl are unsubstituted.

7. A congener of portimine of the structure:

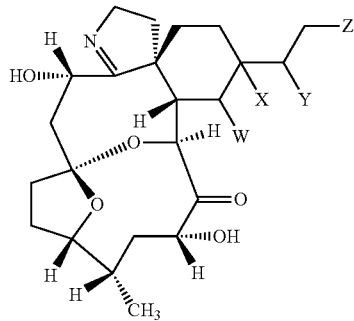

where: W and X form a bond, an epoxide, or are independently selected from the group consisting of: H, halogen, OH and OCOAlkyl; Y and Z form a bond, an epoxide, or are independently selected from the group consisting of: H, halogen, OH and OCOAlkyl; and W and X or Y and Z do not form a bond.

8. The congener of claim 1 where the congener is semi synthetic.

9. The congener of claim 1 where the congener is differentially toxic.

10. The congener of claim 1 where the congener is a differentially toxic, semisynthetic congener.

11. A pharmaceutical preparation comprising as active ingredient a congener of claim 1.

12. The pharmaceutical preparation of claim 11 where the pharmaceutical preparation is indicated for use in the treatment of subjects with neoplasia.

13. The pharmaceutical preparation of claim 12 where the pharmaceutical preparation is indicated for use in the treatment of subjects with lymphoid malignancies.

14. A method of treating a subject with neoplasia comprising the step of administering to the subject an effective amount of portimine or a congener of claim 1.

15. The method of claim 14 where the administration is in conjunction with the administration to the subject of an antagonist of antiapoptotic proteins.

16. The method of claim 15 where the antagonist of antiapoptotic proteins is a BH3 mimetic.

17. The method of claim 16 where the antagonist of antiapoptotic proteins is a BH3 mimetic selected from the group consisting of: 4-[4-[[2-(4-chlorophenyl)-4,4-dimethyl-1-cyclohexen-1-yl]methyl]-1-piperazinyl]-N-[[3-nitro-4-[[(tetrahydro-2H-pyran-4-yl)methyl]amino]phenyl]sulfonyl]-2-(1H-pyrrolo [2,3-b]pyridin-5-yloxy)-benzamide; 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl] propyl]amino]-3-[(trifluoromethyl) sulfonyl]phenyl]sulfonyl]-benzamide; 4-[4-[(4'-chloro[1,1'-biphenyl]-2-yl)methyl]-1-piperazinyl]-N-[[4-[[(1R)-3-(dimethylamino)-1-[(phenylthio) methyl] propyl]amino]-3-nitrophenyl]sulfonyl]-benzamide; (R)-5-(4-chlorophenyl)-4-(3-(4-(4-(4-((4-(dimethylamino)-1-(phenylthio)butan-2-yl)amino)-3-nitrophenyl sulfonamido)-phenyl)piperazin-1-yl)phenyl)-1-ethyl-2-methyl-1H-pyrrole-3-carboxylic acid; (R)-5-(4-chlorophenyl)-4-(3-(4-(4-(4-((4-(dimethylamino)-1-(phenylthio)butan-2-yl) amino)-3-nitrophenyl sulfonamido)-phenyl)piperazin-1-yl) phenyl)-1-isopropyl-2-methyl-1H-pyrrole-3-carboxylic acid; (R)-7-(4-(((4-((4-(dimethylamino)-1-(phenylthio)butan-2-yl)-amino)-3-nitrophenyl) sulfonyl)carbamoyl)-2-methylphenyl)-3-(3-(naphthalen-1-yloxy)propyl) pyrazolo [1,5-a]pyridine-2-carboxylic acid; and (R)-7-(4-(((4-((4-(dimethylamino)-1-(phenylthio)butan-2-yl)-amino)-3-nitrophenyl) sulfonyl)carbamoyl)-2,6-dimethylphenyl)-3-(3-(naphthalen-1-yloxy)propyl)pyrazolo[1,5-α]pyridine-2-carboxylic acid.

18. The method of claim 17 where the antagonist of antiapoptotic proteins is the BH3 mimetic 4-[4-[(4'-chloro [1,1'-biphenyl]-2-yl)methyl]-1-piperazinyl]-N-[[4-[[(1R)-3-(dimethylamino)-1-[(phenylthio) methyl] propyl]amino]-3-nitrophenyl]sulfonyl]-benzamide.

* * * * *